US008036396B2

(12) United States Patent
Sakamoto et al.

(10) Patent No.: US 8,036,396 B2
(45) Date of Patent: Oct. 11, 2011

(54) VEHICULAR ACTIVE VIBRATORY NOISE CONTROL APPARATUS

(75) Inventors: Kosuke Sakamoto, Utsunomiya (JP); Toshio Inoue, Shioya-gun (JP); Akira Takahashi, Shioya-gun (JP); Yasunori Kobayashi, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 643 days.

(21) Appl. No.: 12/197,883

(22) Filed: Aug. 25, 2008

(65) Prior Publication Data

US 2009/0060217 A1 Mar. 5, 2009

(30) Foreign Application Priority Data

Sep. 3, 2007 (JP) ................................ 2007-228210

(51) Int. Cl.
*A61F 11/06* (2006.01)
*G10K 11/16* (2006.01)

(52) U.S. Cl. ...................................................... 381/71.4

(58) Field of Classification Search ................. 381/71.1, 381/71.4, 86, 71.11–12
See application file for complete search history.

(56) References Cited

U.S. PATENT DOCUMENTS 5,359,662 A * 10/1994 Yuan et al. ................. 381/71.14
5,802,184 A * 9/1998 Heath .......................... 381/71.4
7,574,006 B2 * 8/2009 Funayama et al. .......... 381/71.12
2004/0258252 A1 * 12/2004 Inoue et al. .................. 381/71.4

FOREIGN PATENT DOCUMENTS

JP 2000-280831 A 10/2000

* cited by examiner

*Primary Examiner* — Tuyen Nguyen
(74) *Attorney, Agent, or Firm* — Arent Fox LLP

(57) ABSTRACT

A vehicular active vibratory noise control apparatus includes an adaptive notch filter (second control signal generating unit) for generating a corrected error signal representative of a road noise only by removing the component of a rotational frequency (the component of an engine muffled sound) from an error signal, generates a first control signal from the corrected error signal and a reference signal, and reduces the component of the rotational frequency (engine muffled sound) at a position where a microphone is located (evaluating point).

5 Claims, 13 Drawing Sheets

FIG. 9A

98

| fe | N1 | N2 | N3 |
|---|---|---|---|
| LOW | 1.5 | 3 | 6 |
| HIGH | 1 | 3 | 6 |

FIG. 9B

98B

| | | N1 | N2 | N3 |
|---|---|---|---|---|
| LOW | fe | 1.5 | 3 | 6 |
| | fp | – | – | – |
| HIGH | fe | – | 3 | 6 |
| | fp | 1 | – | – |

VEHICULAR ACTIVE VIBRATORY NOISE CONTROL APPARATUS

BACKGROUND OF THE INVENTION

1. Field of the Invention

The present invention relates to a vehicular active vibratory noise control apparatus for canceling a road noise by causing a canceling sound that is in opposite phase with the road noise to interfere with the road noise.

2. Description of the Related Art

Heretofore, there has been proposed in the art an active noise control (ANC) apparatus for canceling a road noise (also called "drumming noise") in the passenger's compartment of a vehicle with a canceling sound that is in opposite phase with the road noise at an evaluating point (hearing point) where a microphone is located (see Japanese Laid-Open Patent Publication No. 2000-280831). The road noise is based on the vibrations of vehicle wheels which are caused by the road when the vehicle is running on the road, transferred through the suspensions to the vehicle body, and particularly excited by the acoustic resonant characteristics of the closed room such as a passenger's compartment. The road noise has a peak level at a frequency of about 40 [Hz] and has a frequency bandwidth in the range from 20 to 150 [Hz].

The vehicle has various rotating components including an engine crankshaft, a transmission main shaft, a transmission countershaft, a propeller shaft, etc. which rotate when the engine on the vehicle operates. The rotational frequency of these rotating components varies depending on the speed of the vehicle, etc. When these rotating components rotate, they produce a noise (hereinafter referred to as "engine muffled sound" to be distinguished from the road noise) in the passenger's compartment based on the rotational frequency.

It has been found that when the active noise control apparatus for canceling the road noise is turned on in a frequency range wherein the rotational frequency of the rotating components in the passenger's compartment overlaps the frequency of the road noise, the engine muffled sound caused by the rotation of the rotating components does not change per se, but tends to increase at the evaluating point.

For example, FIG. 12 of the accompanying drawings shows a graph of sound pressures (represented by the vertical axis) measured in the position (evaluating point) of the ears of the driver of a vehicle at different frequencies (represented by the horizontal axis). As shown in FIG. 12, a characteristic curve 2 indicated by the dotted lines is plotted when the road-noise ANC apparatus on the vehicle is turned off, and a characteristic curve 4 indicated by the dot-and-dash lines is plotted when the road-noise ANC apparatus on the vehicle is turned on. As indicated by the characteristic curves 2, 4, at the frequency of 42 [Hz] at which the sound pressure of the road noise is maximum, the sound pressure is lower by 10 [dB] or more when the road-noise ANC apparatus is turned on than when the road-noise ANC apparatus is turned off. However, at the frequency of 65 [Hz] which corresponds to the rotational frequency, the sound pressure is higher by about 5 [dB] when the road-noise ANC apparatus is turned on than when the road-noise ANC apparatus is turned off. The road-noise ANC apparatus is disadvantageous in that while it can reduce the road noise, it tends to increase the engine muffled sound at the frequency of 65 [Hz].

Furthermore, as shown in FIG. 13 of the accompanying drawings, if the rotational frequency is of about 45 [Hz], then a characteristic curve 6 indicated by the dotted lines is plotted when the road-noise ANC apparatus is turned off, and a characteristic curve 8 indicated by the dot-and-dash lines is plotted when the road-noise ANC apparatus is turned on. The comparison of these characteristic curves 6, 8 shows that the road-noise ANC apparatus is not effective to lower the sound pressure at the rotational frequency of about 45 [Hz].

SUMMARY OF THE INVENTION

It is an object of the present invention to provide a vehicular active vibratory noise control apparatus which is capable of greatly reducing an increase in an engine muffled sound that is generated at the rotational frequency of rotating components or harmonic frequencies thereof, at a hearing point at the time an ANC apparatus for canceling a road noise is turned on.

A vehicular active vibratory noise control apparatus according to the present invention includes a first standard signal generator for generating a first standard signal relative to a road noise on a vehicle, a first adaptive filter for outputting a first control signal based on the first standard signal, a canceling sound output unit for outputting a canceling sound to cancel the road noise based on the first control signal, an error signal detector for detecting a residual noise due to an interference between the canceling sound and the road noise at an evaluating point as an error signal, and a first filter coefficient updater for sequentially updating a first filter coefficient of the first adaptive filter.

The vehicular active vibratory noise control apparatus also includes a rotational frequency detector for detecting a rotational frequency of a rotating component mounted on the vehicle, a second standard signal generator for generating a second standard signal relative to the rotating component based on the detected rotational frequency, a second adaptive filter for outputting a second control signal based on the second standard signal, a second filter coefficient updater for sequentially updating a second filter coefficient of the second adaptive filter, and a subtractor for generating a corrected error signal by subtracting the second control signal from the error signal. The first filter coefficient updater updates the first filter coefficient based on the corrected error signal and the first standard signal.

According to the present invention, the first control signal is generated from the corrected error signal representative of only the component of the road noise that is produced by removing the component of the rotational frequency from the error signal. Therefore, the component of the rotational frequency is greatly reduced at the evaluating point. As a result, an increase in an engine muffled sound generated depending on the rotational frequency of the rotating component, which becomes evident at the evaluating point when a road-noise ANC is turned on, is greatly reduced.

The rotating component comprises at least one of an engine crankshaft, a transmission main shaft, a transmission countershaft, a drive shaft, and a propeller shaft on the vehicle.

The second control signal stops being output based on the rotational frequency. Accordingly, the vehicular active vibratory noise control apparatus operates only in a frequency range which requires noise control.

The rotational frequency detector detects the rotational frequencies of a plurality of rotating components, and the second standard signal generator generates a plurality of second standard signals based on the detected rotational frequencies. Therefore, an increase in engine muffled sounds is reduced at the rotational frequencies of the plural rotating components, e.g., the engine crankshaft and the propeller shaft.

According to the present invention, consequently, an increase in an engine muffled sound generated depending on the rotational frequency of the rotating component, which becomes evident at the evaluating point when a road-noise ANC is turned on, is greatly reduced.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 9A is a diagram showing a table of rotational frequencies and multiplication numbers which is applied to the vehicular active vibratory noise control apparatus shown in FIG. 8;

FIG. 9B is a diagram showing a table of rotational frequencies and multiplication numbers which is applied to a vehicular active vibratory noise control apparatus shown in FIG. 10;

DESCRIPTION OF THE PREFERRED EMBODIMENTS

Figure 1:
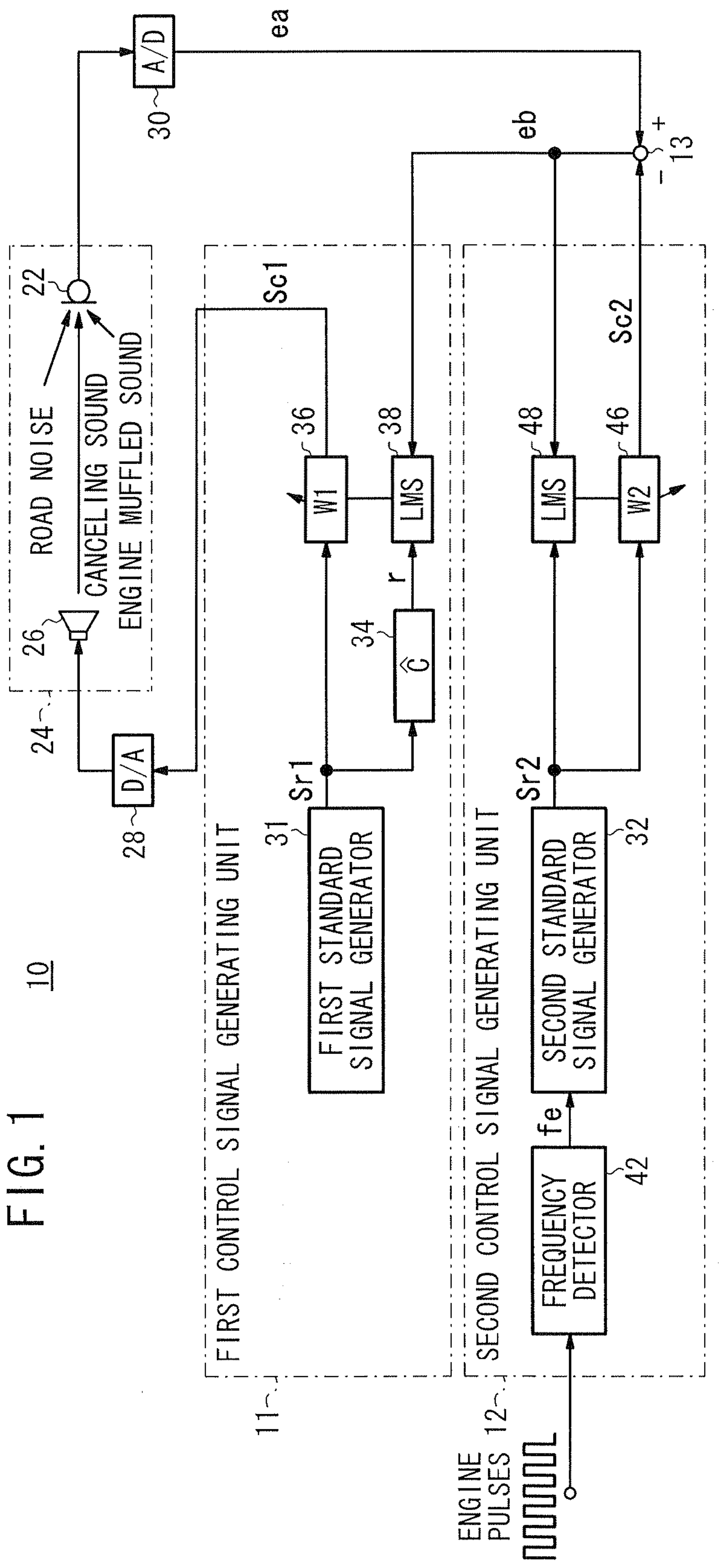
FIG. 1 is a block diagram showing a general configuration of a vehicular active vibratory noise control apparatus according to an embodiment of the present invention.

Like or corresponding reference characters denote like or corresponding parts throughout views.

Figure 2:
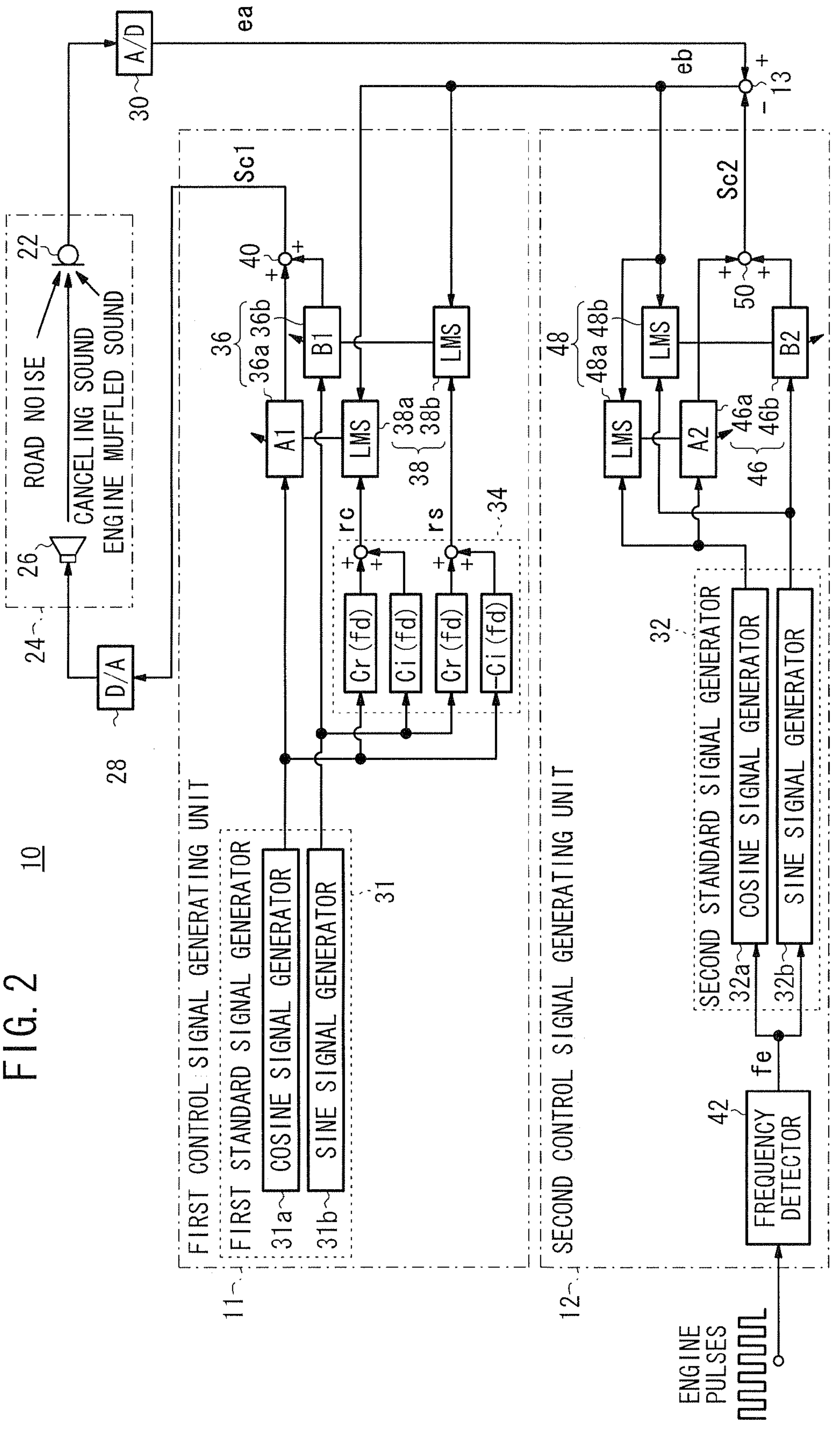
FIG. 2 is a block diagram showing a detailed configuration of the vehicular active vibratory noise control apparatus shown in FIG. 1.

FIG. 1 shows in block form a general configuration of a vehicular active vibratory control noise (ANC) apparatus 10 according to an embodiment of the present invention, and FIG. 2 shows in block form a detailed configuration of the vehicular active vibratory noise control apparatus 10 shown in FIG. 1.

As shown in FIGS. 1 and 2, the vehicular active vibratory noise control apparatus 10 basically comprises a first control signal generating unit 11 for generating a first control signal Sc1 for producing a canceling sound to cancel a road noise, a second control signal generating unit 12 for generating a second control signal Sc2 which is of the same amplitude as and in phase with the component of an engine muffled sound in an error signal ea, to be described later, and a subtractor 13 for generating a corrected error signal eb representative of a road noise only by subtracting the second control signal Sc2 from the error signal ea and supplying the corrected error signal eb to the first and second control signal generating units 11, 12.

The first and second control signal generating units 11, 12 include a computer and operate as function realizing means for realizing various functions when the CPU of the computer executes programs stored in a memory such as a ROM or the like based on various input signals applied thereto.

A microphone (error signal detector) 22 serves to detect a residual noise due to an interference between an engine muffled sound, a road noise, and a canceling sound for the road noise as an error signal at an evaluating point (an evaluating position, a hearing point). The microphone 22 is disposed at the position of an antinode in a primary or secondary mode of an acoustic inherent mode in the longitudinal direction of an in-compartment space 24 (the position where the sound pressure of the standing wave of a resonant in-compartment sound at 42 [Hz] or 84 [Hz], of the road noise in a bandwidth from 20 to 150 Hz, is large}. Specifically, if the vehicle is a sedan, then the microphone 22 is located in a position in a front portion of the vehicle, e.g., near a foot space in front of a front seat, near a room mirror, or behind an instrumental panel, in a closed space represented by a transverse cross-sectional shape of the vehicle.

A speaker (canceling sound output unit) 26 outputs the canceling sound for canceling the road noise based on the first control signal Sc1 that is supplied from the first control signal generating unit 11 through a D/A converter 28, to the in-compartment space 24. The speaker 26 is disposed in a position on lateral kick panels near the front seat, below the center of the instrumental panel, or on lateral body panels below C pillars near a rear seat of the vehicle, to enhance the 5 ch surround-sound effects. A woofer for 0.1 ch is disposed in any arbitrary position as the sound radiated from the woofer is not directional.

The error signal ea is output from the microphone 22 and converted by an A/D converter 30 into a digital error signal ea, which is supplied to the minuend input port of the subtractor 13.

The subtrahend input port of the subtractor 13 is supplied with the second control signal Sc2 which is of the same amplitude as and in phase with the component of the engine muffled sound in the error signal ea.

The subtractor 13 outputs the corrected error signal eb that is produced by subtracting the second control signal Sc2 from the error signal ea.

The corrected error signal eb is supplied to the first control signal generating unit 11 which functions as an active noise control (ANC) apparatus.

The first control signal generating unit 11 is a circuit utilizing a feed-forward filtered-X LMS (Least Mean Square) algorithm. The first control signal generating unit 11 comprises a first standard signal generator 31 (a cosine signal generator 31*a* and a sine signal generator 31*b*) for generating a first standard signal Sr1 {a cosine signal cos(2πfdt) and a sine signal sin(2πfdt)} inherent in the type of the vehicle, e.g., in synchronism with a road noise frequency fd [Hz] of about 42 [Hz], a reference signal generator (filter) 34 for setting therein a simulated transfer function C^ {a simulated transfer function (real part) Cr(fd) and a simulated transfer function (imaginary part) Ci(fd)} which simulates the transfer characteristics of the sound having the road noise frequency fd in the in-compartment space 24 from the speaker 26 to the microphone 22, and processing (correcting or filtering) the cosine signal cos(2πfdt) and the sine signal sin(2πfdt) into a reference signal r {a reference signal rc as a simulated cosine signal and a reference signal rs as a simulated sine signal), a filter coefficient updater (algorithm processor) 38 {38*a*, 38*b*} for being supplied with the reference signals rc, rs and the corrected error signal eb and updating filter coefficients A1, B1 of a first adaptive filter 36 (an adaptive filter 36*a* and an adaptive filter 36*b*) which is a one-tape adaptive filter, based on an adaptive control algorithm for minimizing the corrected error signal eb, e.g., an LMS (Least Mean Square) algorithm which is a type of steepest descent method, and an adder 40 (see FIG. 2) for adding a cosine signal A1×cos(2πfdt), which has been multiplied by the filter coefficient A1, and a sine signal B1×sin(2πfdt), which has been multiplied by the filter coefficient B1, both supplied from the first adaptive filter 36 (36*a*, 36*b*), to generate the first control signal Sc1 {Sc1=A1×cos(2πfdt)+B1×sin(2πfdt)}.

In FIG. 1, the filter coefficient A1 and the filter coefficient B1 are expressed altogether as a filter coefficient W1, and the first control signal Sc1 is expressed as Sc1=W1×Sr1.

The second control signal generating unit 12 includes adaptive notch filters which functions as bandpass filters (BPF).

The second control signal generating unit 12 comprises a frequency detector (rotational frequency detector) 42, which is a frequency counter, for detecting the rotational frequency fe of an engine crankshaft (rotating component) from an engine rotation signal (engine pulses) supplied from a fuel injection ECU (FIECU), not shown, a second standard signal generator 32 {a cosine signal generator 32*a* and a sine signal generator 32*b*} for generating a second standard signal Sr2 {a cosine signal cos(2πfet) and a sine signal sin(2πfet)} having the rotational frequency fe, a filter coefficient updater (algorithm processor) 48 (48*a*, 48*b*) for being supplied with the second standard signal Sr2 {the cosine signal cos(2πfet) and the sine signal sin(2πfet)} and the corrected error signal eb and updating a filter coefficient W2 (A2, B2) of a second adaptive filter 46 (an adaptive filter 46*a* and an adaptive filter 46*b*) which is a one-tape adaptive filter, based on an adaptive control algorithm for minimizing the corrected error signal eb, e.g., an LMS (Least Mean Square) algorithm which is a type of steepest descent method, and an adder 50 (see FIG. 2) for adding a cosine signal A2'cos(2πfet), which has been multiplied by the filter coefficient A2, and a sine signal B2×sin(2πfet), which has been multiplied by the filter coefficient B2, both supplied from the second adaptive filter 46 (46*a*, 46*b*), to generate the second control signal Sc2{Sc2=A2×cos(2πfet)+B2×sin(2πfet)}.

In FIG. 1, the filter coefficient A2 and the filter coefficient B2 are expressed altogether as a filter coefficient W2, and the second control signal Sc2 is expressed as Sc2=W2×Sr2.

The subtractor 13 supplies the corrected error signal eb, which is produced by subtracting the second control signal Sc2 from the error signal ea, to the filter coefficient updater 38 {38*a*, 38*b*} of the first control signal generating unit 11 and the filter coefficient updater 48 (48*a*, 48*b*) of the second control signal generating unit 12.

The vehicular active vibratory noise control apparatus 10 is basically constructed as described above. Operation of the vehicular active vibratory noise control apparatus 10 will be described below.

The microphone 22 detects a residual noise due to an interference between a road noise, a canceling sound supplied from the speaker 26 for canceling the road noise, and an engine muffled sound, as an error signal ea. The error signal ea is converted by the A/D converter 30 into a digital error signal ea, which is supplied to the minuend input port of the subtractor 13.

The second control signal generating unit 12 operates to determine the filter coefficient W2 (A2, B2) of the second adaptive filter 46 (46*a*, 46*b*) in order to minimize the corrected error signal eb that is input to the filter coefficient updater 48 (48*a*, 48*b*). Therefore, the subtrahend input port of the subtractor 13 is supplied with the second control signal Sc2 which is of the same amplitude as and in phase with the component of the rotational frequency fe (the component of the engine muffled sound) in the error signal ea.

Specifically, the second control signal generating unit 12 functions as a notch filter having the central frequency fe on the output side of the subtractor 13 (where the corrected error signal eb is generated), and functions as a bandpass filter (BPF) having the central frequency fe on the input side of the subtractor 13 (where the control signal Sc2 is generated). The bandpass characteristics (steepness) of the bandpass filter can be changed by adjusting a step size parameter as a control parameter.

The filter coefficient W2 is updated according to the following equation (1):

$$W2(n+1)=W2(n)-\mu\cdot eb(n)\cdot Srn(n) \tag{1}$$

where μ represents the step size parameter and n represents the sampling time.

Therefore, the corrected error signal eb contains only an error signal component having the frequency fd=42 [Hz] due to the interference between the road noise and the canceling sound therefor, the error signal component being produced by subtracting the component of the engine muffled sound from the error signal ea.

The first control signal generating unit 11 operates to determine the filter coefficient W1 (A1, B1) in order to minimize the corrected error signal eb based on the reference signal r (r=rc, rs) and the corrected error signal eb, and generates the first control signal Sc1. The first control signal Sc1 is supplied through the D/A converter 28 to the speaker 26, and then via the in-compartment space 24 to the microphone 22. At the position of the microphone 22, even if the engine muffled sound is present, the residual component due to the interference between the road noise and the canceling sound is minimized.

Figure 3:
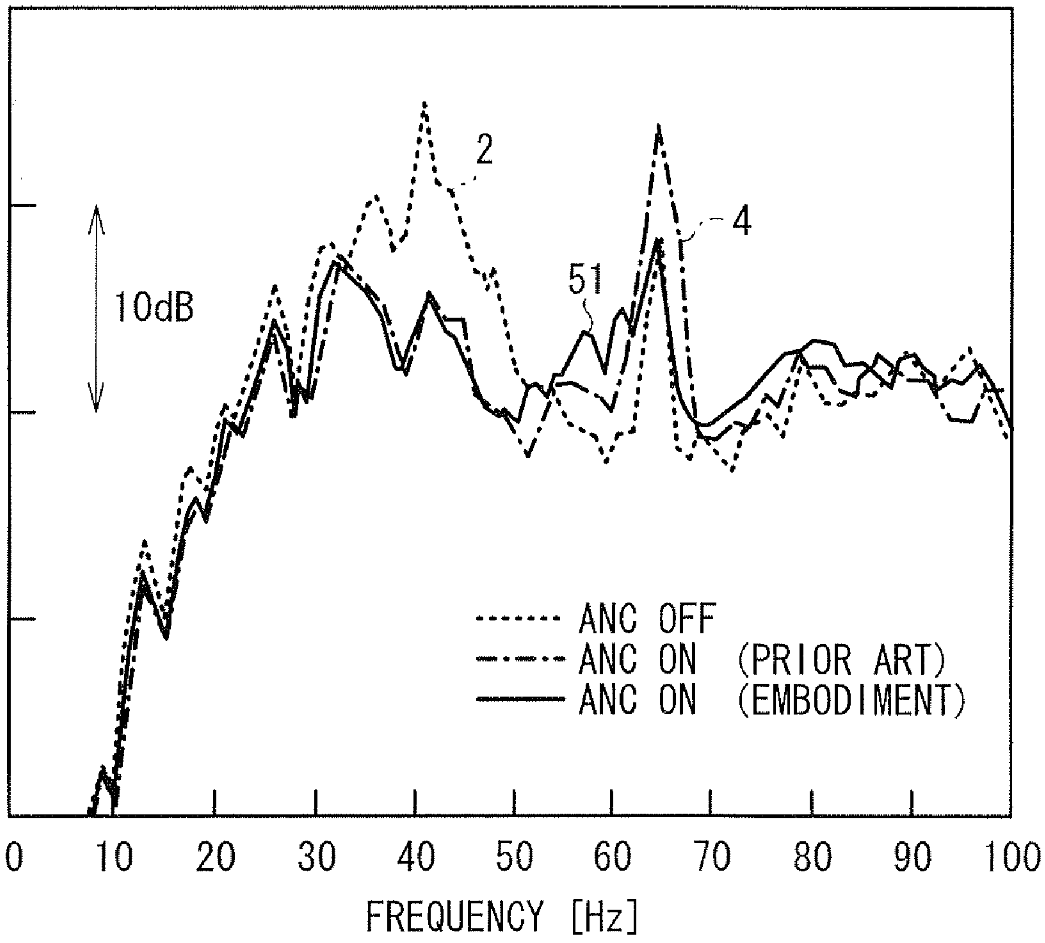
FIG. 3 is a graph showing measured noise reduction effects achieved when an ANC apparatus is turned off, an ANC apparatus (the related art) is turned on, and an ANC apparatus (the embodiment) is turned on at a certain rotational frequency.

FIG. 3 is a graph showing measured noise reduction effects of the vehicular active vibratory noise control apparatus 10 according to the present embodiment at the time the rotational frequency fe of the engine crankshaft is fe 65 [Hz]. The graph has a horizontal axis representative of the frequency and a vertical axis representative of the sound pressure at the position of the microphone 22 (evaluating point). In FIG. 3, a characteristic curve 2 (which is the same as the characteristic curve 2 shown in FIG. 12) indicated by the dotted lines is plotted when the ANC apparatus according to the related art is turned off, and a characteristic curve 4 (which is the same as the characteristic curve 4 shown in FIG. 12) indicated by the dot-and-dash lines is plotted when the ANC apparatus according to the related art is turned on. As indicated by the characteristic curves 2, 4, at the frequency of 42 [Hz] at which the sound pressure of the road noise is maximum, the sound pressure is lower by 10 [dB] or more when the ANC apparatus is turned on than when the ANC apparatus is turned off. However, at the frequency of 65 [Hz] which corresponds to the rotational frequency fe of the engine crankshaft, the sound pressure is higher (becomes more evident) by about 5 [dB] when the ANC apparatus is turned on than when the ANC apparatus is turned off. The ANC apparatus is disadvantageous in that while it can reduce the road noise at the evaluating point, it tends to increase the engine muffled sound at the evaluating point. FIG. 3 also shows a characteristic curve 51 indicated by the solid lines which is plotted when the vehicular active vibratory noise control apparatus 10 is turned on. The characteristic curve 51 indicates that the sound pressure is prevented from being greatly increased at the frequency of 65 [Hz] which corresponds to the rotational frequency fe of the engine crankshaft (rotating component).

Figure 4:
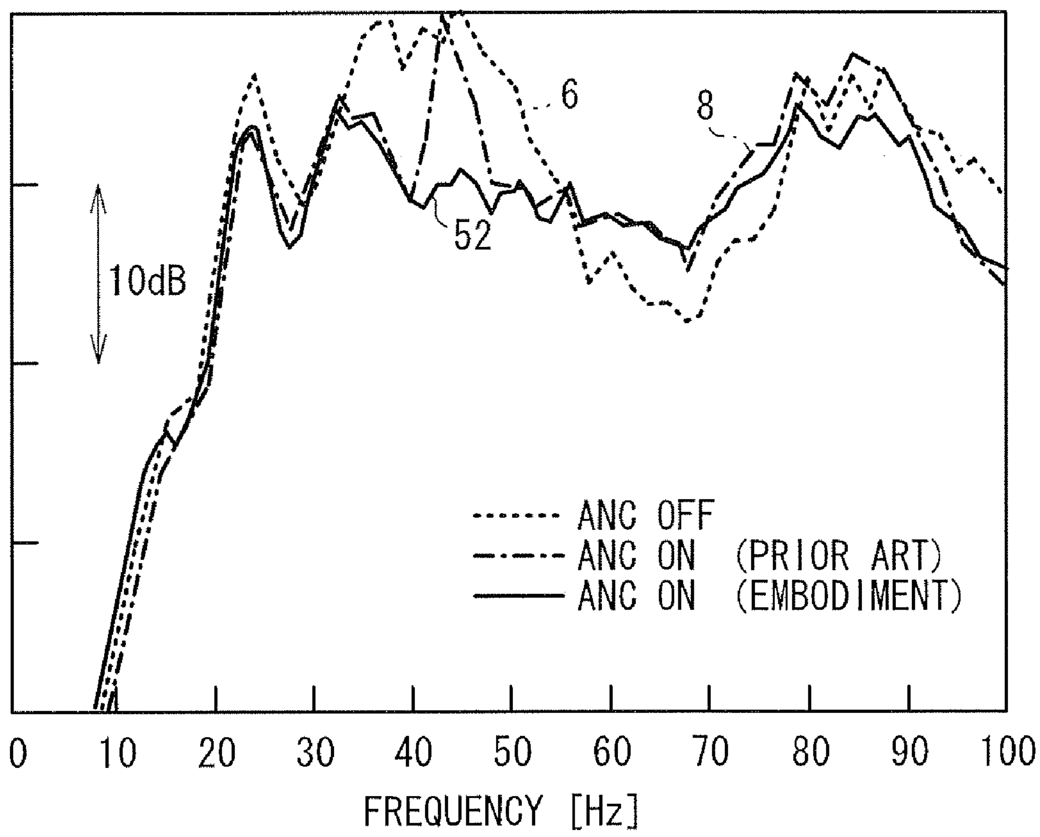
FIG. 4 is a graph showing measured noise reduction effects achieved when the ANC apparatus is turned off, the ANC apparatus (the related art) is turned on, and the ANC apparatus (the embodiment) is turned on at another rotational frequency.
Figure 13:
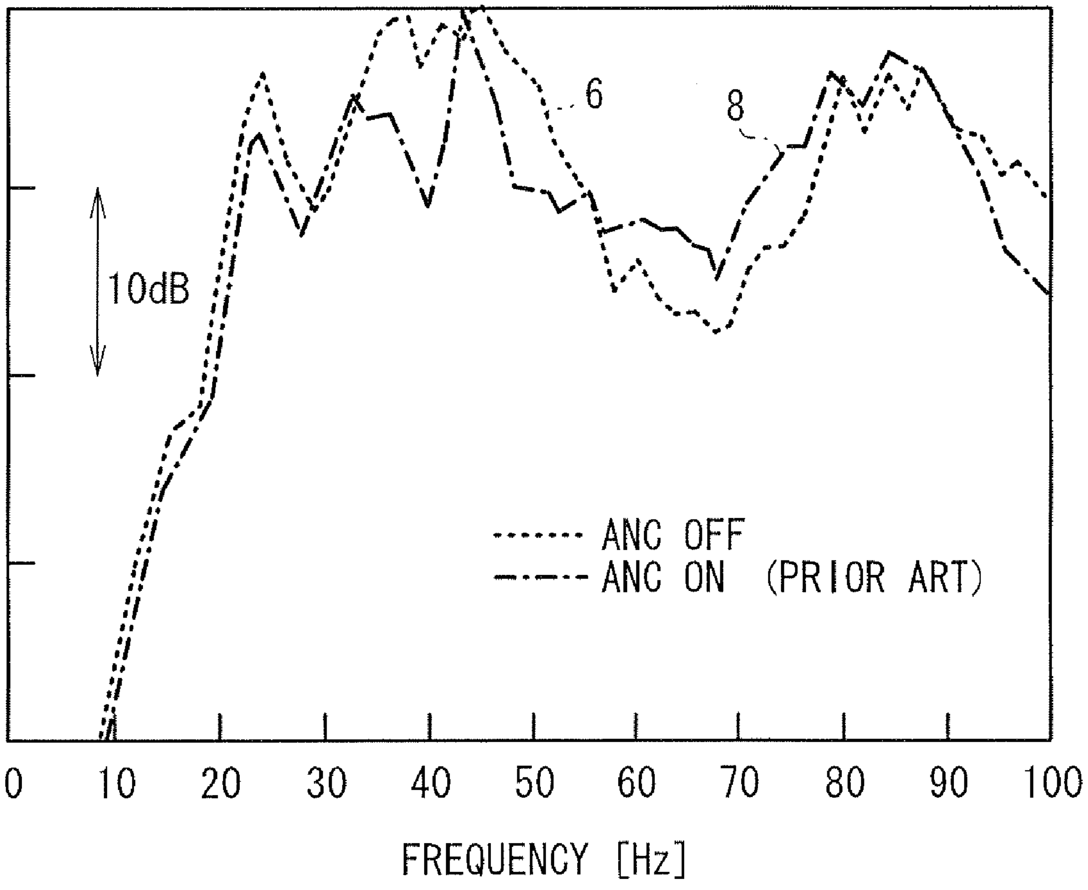
FIG. 13 is a graph showing measured a noise reduction effect achieved when the ANC apparatus (the related art) is turned off and the ANC apparatus (the related art) is turned on at another rotational frequency.

FIG. 4 is a graph showing measured noise reduction effects of the vehicular active vibratory noise control apparatus 10 according to the present embodiment at the time the rotational frequency fe of the engine crankshaft is fe=45 [Hz]. The graph has a horizontal axis representative of the frequency and a vertical axis representative of the sound pressure at the position (evaluating point) of the microphone 22 (evaluating point). In FIG. 4, a characteristic curve 6 (which is the same as the characteristic curve 6 shown in FIG. 13) indicated by the dotted lines is plotted when the ANC apparatus according to the related art is turned off, and a characteristic curve 8 (which is the same as the characteristic curve 8 shown in FIG. 13) indicated by the dot-and-dash lines is plotted when the ANC apparatus according to the related art is turned on. A comparison of the characteristic curves 6, 8 shows that the ANC apparatus according to the related art is not effective to lower the sound pressure at the rotational frequency of about 45 [Hz]. FIG. 4 also shows a characteristic curve 52 indicated by the solid lines which is plotted when the vehicular active vibratory noise control apparatus 10 is turned on. The characteristic curve 52 indicates that the sound pressure is completely prevented from being increased at the frequency of 45 [Hz].

As described above, the vehicular active vibratory noise control apparatus 10 according to the present embodiment includes the first standard signal generator 31 for generating the first standard signal Sr1 relative to the road noise, the first adaptive filter 36 for outputting the first control signal Sc1 based on the first standard signal Sr1, the speaker (canceling sound output unit) 26 for outputting a canceling sound to cancel the road noise based on the first control signal Sc1, the microphone (error signal detector) 22 for detecting a residual noise due to the interference between the canceling sound and the road noise at the evaluating point as the error signal ea, the first filter coefficient updater 38 for sequentially updating the first filter coefficient W1 of the first adaptive filter 36, the frequency detector (rotational frequency detector) 42 for detecting the rotational frequency fe of the rotating component on the vehicle, the second standard signal generator 32 for generating the second standard signal Sr2 relative to the rotating component based on the detected rotational frequency fe, the second adaptive filter 46 for outputting the second control signal Sc2 based on the second standard signal Sr2, the second filter coefficient updater 48 for sequentially updating the second filter coefficient W2 of the second adaptive filter 46, and the subtractor 13 for generating the corrected error signal eb by subtracting the second control signal Sc2 from the error signal ea. The first filter coefficient updater 38 updates the first filter coefficient W1 based on the corrected error signal eb and the reference signal r which is produced when the first reference signal Sr1 is filtered by the reference signal generator 34.

With the above arrangement, since the first control signal Sc1 is generated only based on the corrected error signal eb representative of the road noise component which is produced by removing the component of the rotational frequency fe (the component of the engine muffled sound) from the error signal ea, the component of the rotational frequency can greatly be reduced at the position where the microphone 22 is located (the evaluating point). As a result, the engine muffled sound produced at the rotational frequency fe of the rotating component (the engine crankshaft 64 in the present embodiment), which becomes more evident at the evaluating point when the road-noise ANC apparatus according to the related art is turned on, is greatly reduced.

Figure 12:
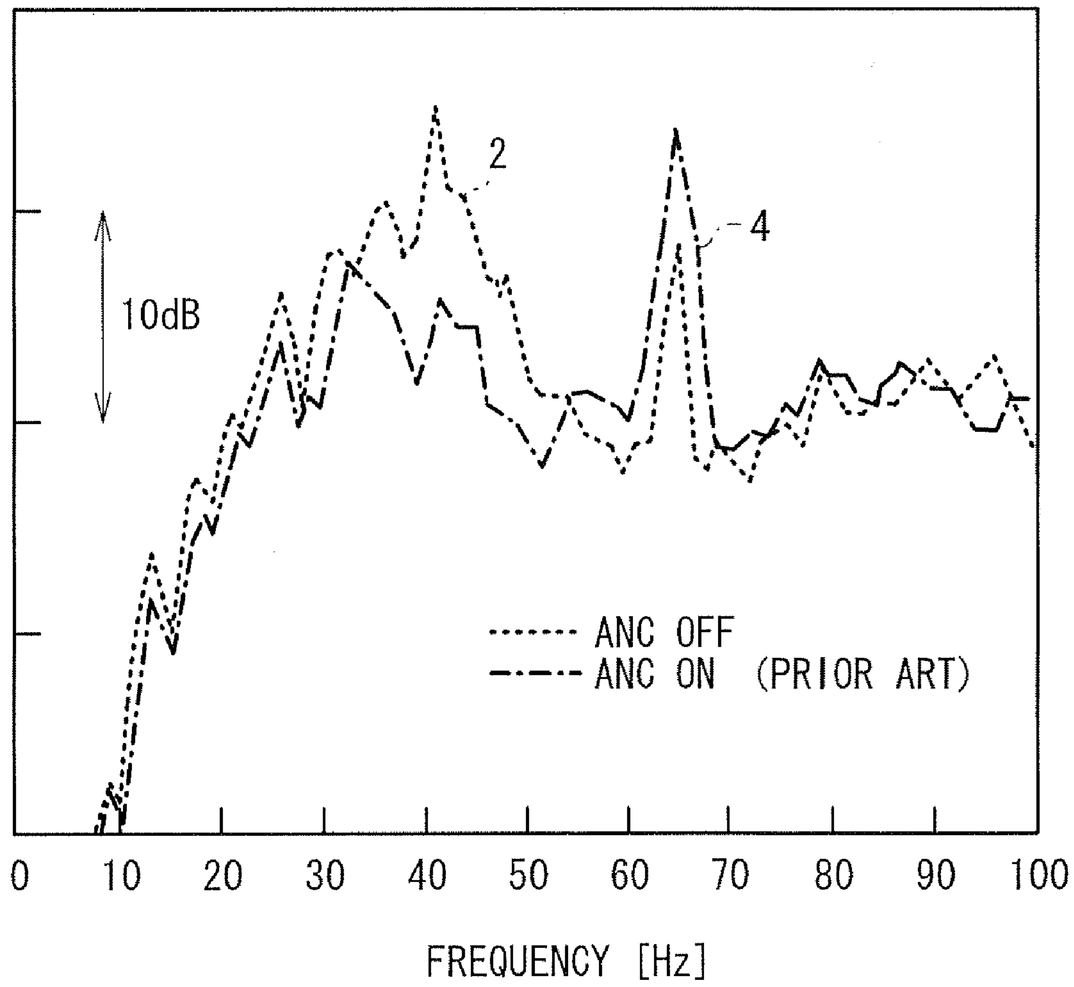
FIG. 12 is a graph showing measured a noise reduction effect achieved when an ANC apparatus (the related art) is turned off and the ANC apparatus (the related art) is turned on at a certain rotational frequency.

Stated otherwise, the road-noise ANC apparatus according to the related art is different from the vehicular active vibratory noise control apparatus 10 according to the present embodiment shown in FIGS. 1 and 2 in that it lacks the second control signal generating unit 12 and the subtractor 13 and the error signal ea output from the A/D converter 30 is directly supplied to the filter coefficient updater 38 of the first control signal generating unit 11. When the ANC apparatus is turned on, the sound pressure is reduced by about 10 [dB] at frequency fd=42 [Hz] of the road noise, as shown in FIG. 12 (FIG. 3). However, the gain is increased at the frequency of 65 [Hz]. If the rotational frequency fe of the engine crankshaft becomes synchronous with the frequency of 65 [Hz], then the engine muffled sound becomes evident at the frequency synchronous with the rotational frequency fe as indicated by the characteristic curve 4 shown in FIG. 12 (FIG. 3). The engine muffled sound at the frequency synchronous with the rotational frequency fe can be reduced (the effect of the engine muffled sound can be reduced) as indicated by the characteristic curve 51 by providing the second control signal generating unit 12 and the subtractor 13 shown in FIGS. 1 and 2 between the output of the A/D converter 30 and the input of the first control signal generating unit 11.

Figure 5:
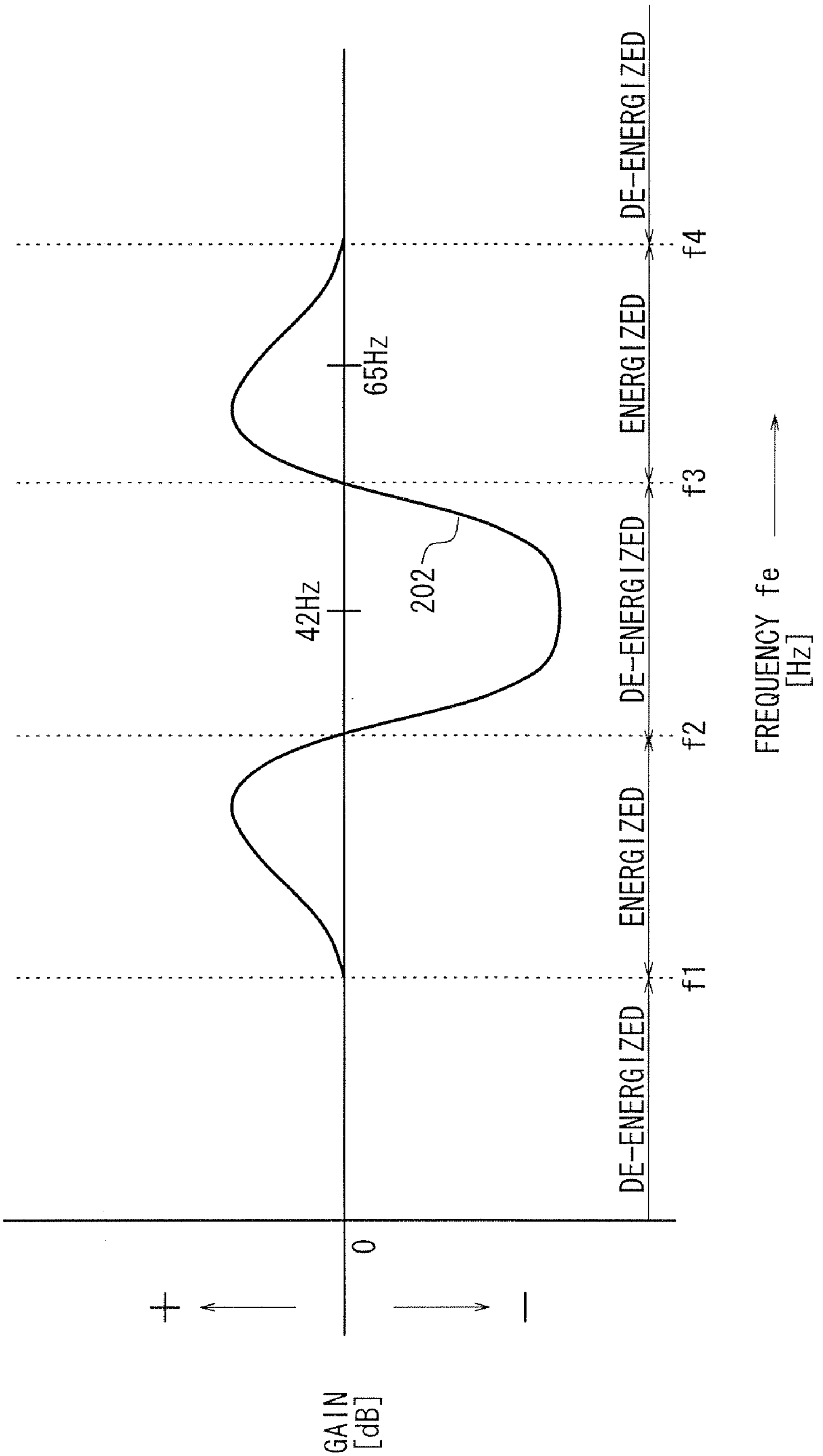
FIG. 5 is a diagram showing sensitivity function characteristics at the time a first control signal generating unit for reducing a road noise produced in the space of a passenger's compartment operates.

FIG. 5 shows a sensitivity function characteristic curve 202 at the time the first control signal generating unit 11 for reducing the road noise produced at the frequency of 42 [Hz] in the in-compartment space 24. the sensitivity function characteristic curve 202 has a negative gain in a frequency range of f2 to f3 about the frequency fd =42 [Hz] of the road noise, and a positive gain in adjacent frequency ranges of f1 to f2 and f3 to f4 (including the frequency of 65 [Hz]).

The second control signal generating unit 12 for reducing the engine muffled sound can be operated only in frequency ranges which need control over the engine muffled sound, i.e., de-energized in the frequency range of f0 to f1, energized in the frequency range of f1 to f2, de-energized in the frequency range of f2 to f3, energized in the frequency range of f3 to f4, and de-energized in a frequency range higher than the frequency f4.

Figure 6:
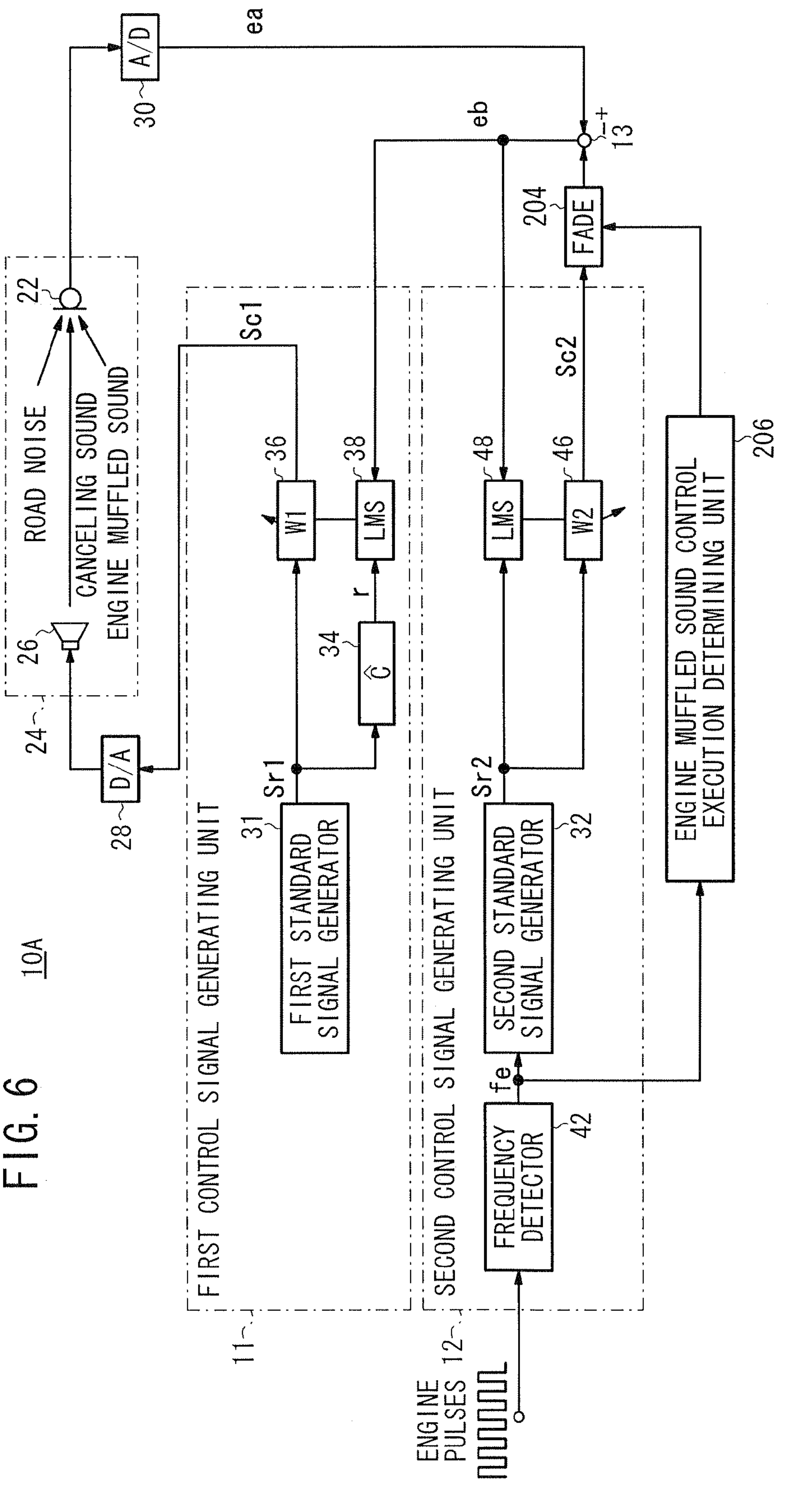
FIG. 6 is a block diagram showing a configuration of a vehicular active vibratory noise control apparatus having a function to selectively activate and inactivate the outputting of a second control signal based on a rotational frequency.

FIG. 6 shows in block form a vehicular active vibratory noise control apparatus 10A having a function to selectively activate and inactivate the outputting of the second control signal Sc2 based on the rotational frequency fe.

The vehicular active vibratory noise control apparatus 10A includes an amplitude controller (gain controller) 204 for controlling the amplitude (gain) of the second control signal Sc2, connected between the second adaptive filter 46 and the subtractor 13. The amplitude controller 204 is selectively turned on and off by an engine muffled sound control execution determining unit 206 based on the rotational frequency fe. If the gain of the amplitude controller 204 is represented by FADE, then it is set to FADE=1 in the energizing frequency ranges of f1 to f2, f3 to f4. In the de-energizing frequency ranges of 0 to f1, f2 to f3, f4 and higher, FADE is progressively reduced according to the following equation (2):

$$FADE(n) = FADE(n-1) \times \text{a constant smaller than 1, for example,} = FADE(n-1) \times 0.9 \quad (2)$$

where n represents the sampling time.

According to a modification, the amplitude controller 204 may be dispensed with, and the filter coefficient W2 of the second adaptive filter 46 may be progressively reduced based on the output signal from the engine muffled sound control execution determining unit 206 in the de-energizing frequency ranges, according to the equation: W2(n)=W2(n−1)×0.9.

Other embodiments of the present invention will be described below.

Figure 7:
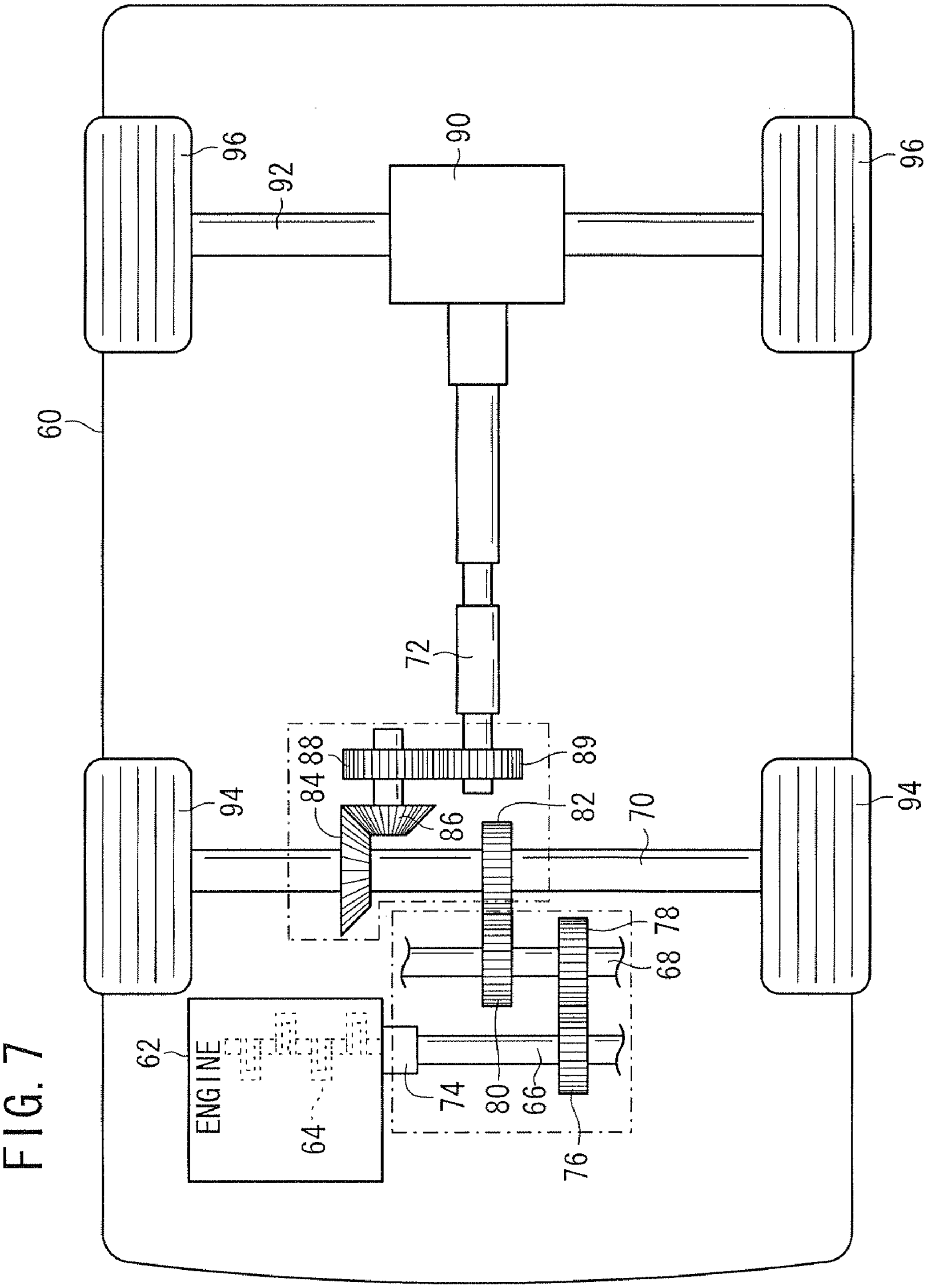
FIG. 7 is a plan view of rotating components on a vehicle.

Actually, various engine muffled sounds generated on a 4WD vehicle 60 shown in FIG. 7. They include a muffled sound produced due to the rotational frequency fe of an engine crankshaft 64 as a rotating component of an engine 62, and muffled sounds produced due to the rotational frequency fe of various rotating components including a transmission main shaft 66, a transmission countershaft 68, a drive shaft 70, a propeller shaft 72, etc. These muffled sounds are also referred to as "engine muffled sounds".

The 4WD vehicle 60 shown in FIG. 7 will briefly be described below. The transmission main shaft 66 is operatively connected to the engine 62 through a clutch 74, and the transmission countershaft 68 is operatively connected to the transmission main shaft 66 through transmission gears 76, 78. The drive shaft 70 is operatively connected to the transmission countershaft 68 through final gears 80, 82. The propeller shaft 72 is operatively connected to the drive shaft 70 through bevel gears 84, 86 and transfer gears 88, 89. The propeller shaft 72 causes a rear differential 90 to rotate a drive shaft 92. Front wheels 94 are rotated by the drive shaft 70, and rear wheels 96 are rotated by the drive shaft 92.

As described above, the 4WD vehicle 60 includes many rotating components operatively connected to the engine 62. As shown in FIGS. 1 and 2, the road noise and the engine muffled sounds, which are noises depending on the rotational frequency of the rotating components, are detected by the microphone 22 in the in-compartment space 24. If the engine muffled sounds due to the rotational frequency fex of the rotating components including the transmission main shaft 66, the transmission countershaft 68, the drive shaft 70, the propeller shaft 72, etc., in addition to the engine muffled sounds produced by the engine crankshaft 64, can be removed by the second control signal generating unit 12, then more silence can be achieved in the in-compartment space 24.

The rotational frequency fex of the rotating components including the transmission main shaft 66, the transmission countershaft 68, the drive shaft 70, the propeller shaft 72, etc. is represented by a multiple of the rotational frequency fe of the engine crankshaft 64 by a real number (1.5, 2, etc.) determined by a gear ration. The engine muffled sound due to the rotational frequency of the propeller shaft 72 (propeller shaft muffled sound) is almost unrecognizable when the rotational frequency fe of the engine crankshaft 64 is low, and can only be heard when the rotational frequency fe of the engine crankshaft 64 is high.

Based on the above analysis, it has been found that the engine muffled sounds produced in the 4WD vehicle 60 shown in FIG. 7 can be reduced efficiently in a wide speed range by removing engine muffled sounds of 1.5th, 3rd, and 6th components of the rotational frequency fe at a low speed and removing engine muffled sounds of 1st, 3rd, and 6th components of the rotational frequency fe at a high speed.

Figure 8:
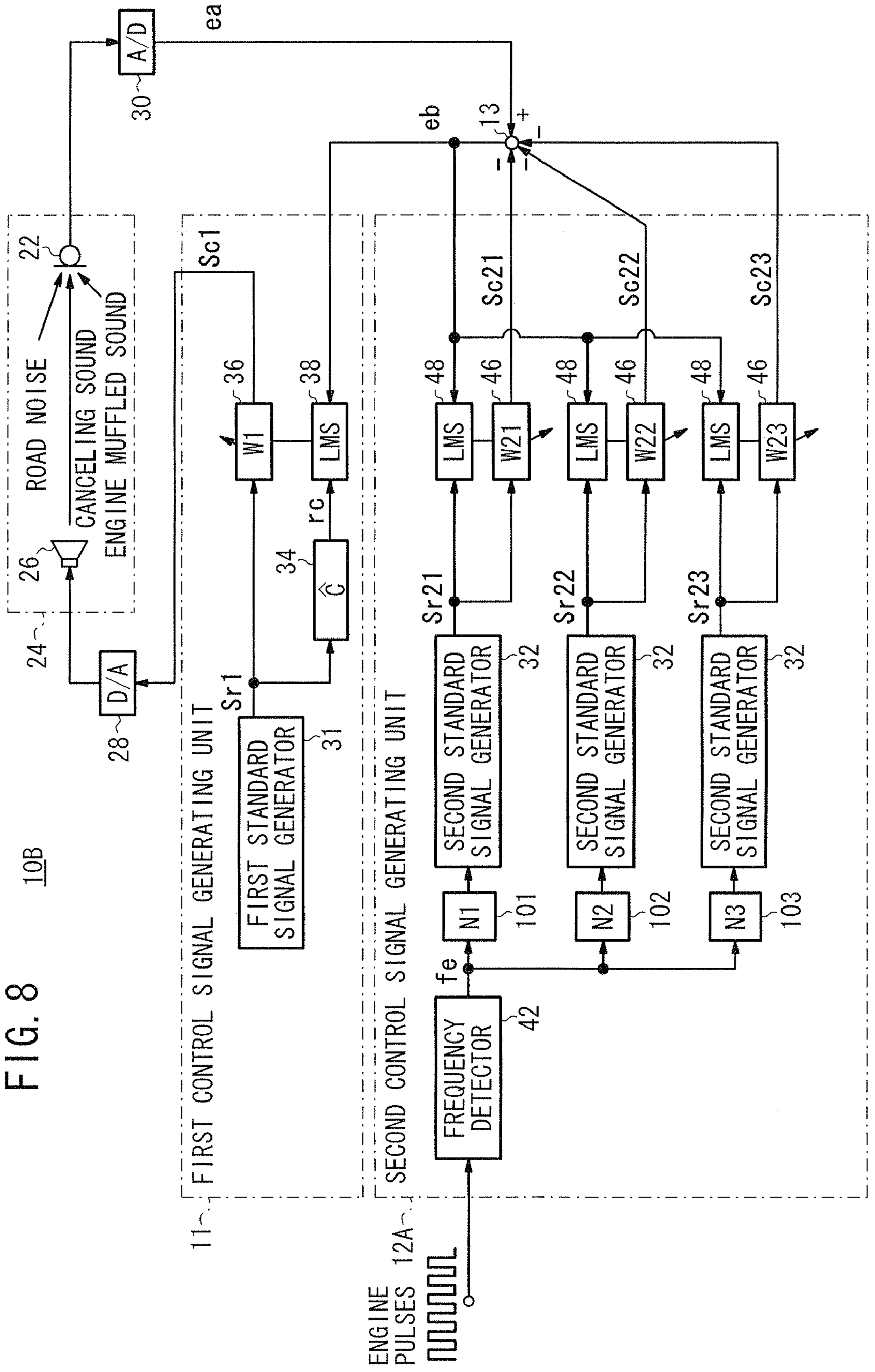
FIG. 8 is a block diagram showing a detailed configuration of a vehicular active vibratory noise control apparatus according to another embodiment of the present invention.

FIG. 8 shows in block form a detailed configuration of a vehicular active vibratory noise control apparatus 10B according to another embodiment of the present invention. The vehicular active vibratory noise control apparatus 10B includes a second control signal generating unit 12 A having three parallel adaptive notch filters whose input terminals are connected to respective multipliers 101, 102, 103 which have respective multiplication numbers N1, N2, N3. When the rotational frequency fe is low, the multiplication numbers N1, N2, N3 of the multipliers 101, 102, 103 are set to N1=1.5, N2=3, and N3=6 based on a table (map) of rotational frequencies and multiplication numbers shown in FIG. 9A. When the rotational frequency fe is high, the multiplication numbers N2, N3 of the multipliers 102, 103 remain unchanged, and only the multiplication number N1 of the multiplier 101 is changed from N1=1.5 to N1=1 based on the table (map) shown in FIG. 9A. In this manner, the vehicular active vibratory noise control apparatus 10B is capable of effectively reducing an increase in the road noise at the frequencies corresponding to the engine muffled sounds in a wide rotational frequency range.

In the second control signal generating unit 12 A, the adaptive notch filters correct three second standard signals Sr21, Sr22, Sr23 output from respective standard signal generators 32 connected to the respective multipliers 101, 102, 103, with three filter coefficients W21, W22, W23 by way of convolution, and output respective second control signals Sc21, Sc22, Sc23. The adaptive notch filters are selectively used depending on whether the rotational frequency fe is high or low. The first control signal generating unit 11 can silence only the road noise with a corrected error signal eb {eb=ea−(Sc21+Sc22+Sc23)} that is produced by the subtractor 13 when it subtracts the three second control signals Sc21, Sc22, Sc23, representative of the engine muffled sounds, from the error signal ea. The vehicular active vibratory noise control apparatus 10B is relatively inexpensive and efficient in operation.

Figure 10:
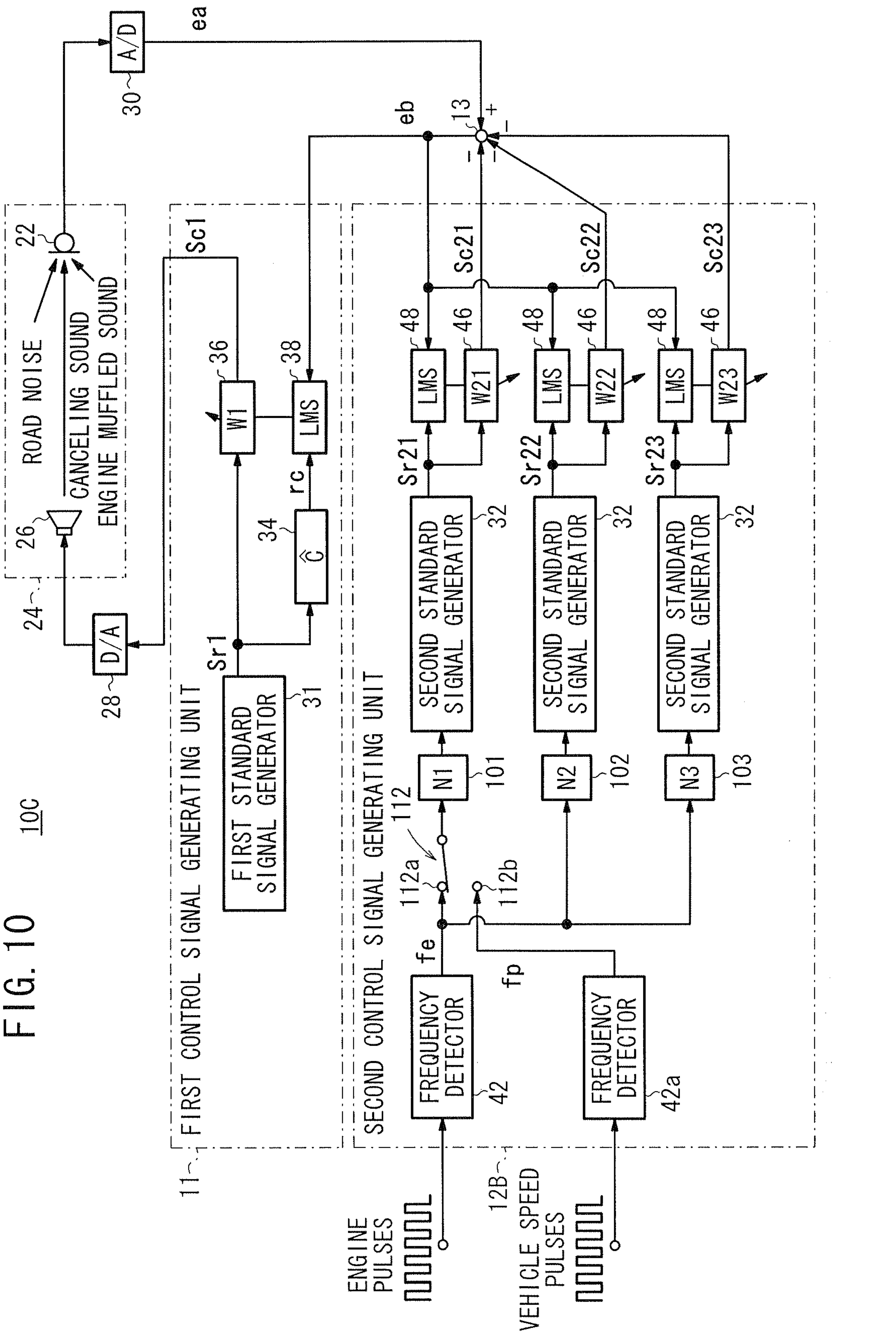
FIG. 10 is a block diagram showing a detailed configuration of a vehicular active vibratory noise control apparatus according to still another embodiment of the present invention.

FIG. 10 shows in block form a vehicular active vibratory noise control apparatus 10C according to still another embodiment of the present invention. The vehicular active vibratory noise control apparatus 10C is based on vehicle-speed-switched control. The vehicular active vibratory noise control apparatus 10C includes a second control signal generating unit 12B having an additional frequency detector 42*a* for detecting the rotational frequency fp of the propeller shaft 72 from vehicle speed pulses, and a selector 112 for selecting the rotational frequency fe of the engine crankshaft 64 or the rotational frequency fp of the propeller shaft 72.

Based on a table (map) of rotational frequencies and multiplication numbers shown in FIG. 9B, when the vehicle speed (in synchronism with the rotational frequency fp) is low, the selector 112 has its movable contact connected to a port 112 a to assign all three resources, i.e., a first resource: the multiplier 101, the second standard signal generator 32, the adaptive filter 46, and the filter coefficient updater 48; a second resource: the multiplier 102, the second standard signal generator 32, the adaptive filter 46, and the filter coefficient updater 48; and a third resource: the multiplier 103, the second standard signal generator 32, the adaptive filter 46, and the filter coefficient updater 48, to the rotational frequency fe of the engine crankshaft 64. When the vehicle speed is high, the selector 112 has its movable contact connected to a port 112*b* to assign the first resource to the rotational frequency fp of the propeller shaft 72 (N1=1) and assign the second and third resources to the rotational frequency fe of the engine crankshaft 64 (N2=3, N3=6). The vehicular active vibratory noise control apparatus 10C is thus capable of reducing the road noise appropriately while preventing the engine muffled sounds from becoming evident when the vehicle speed is high and low.

Figure 11:
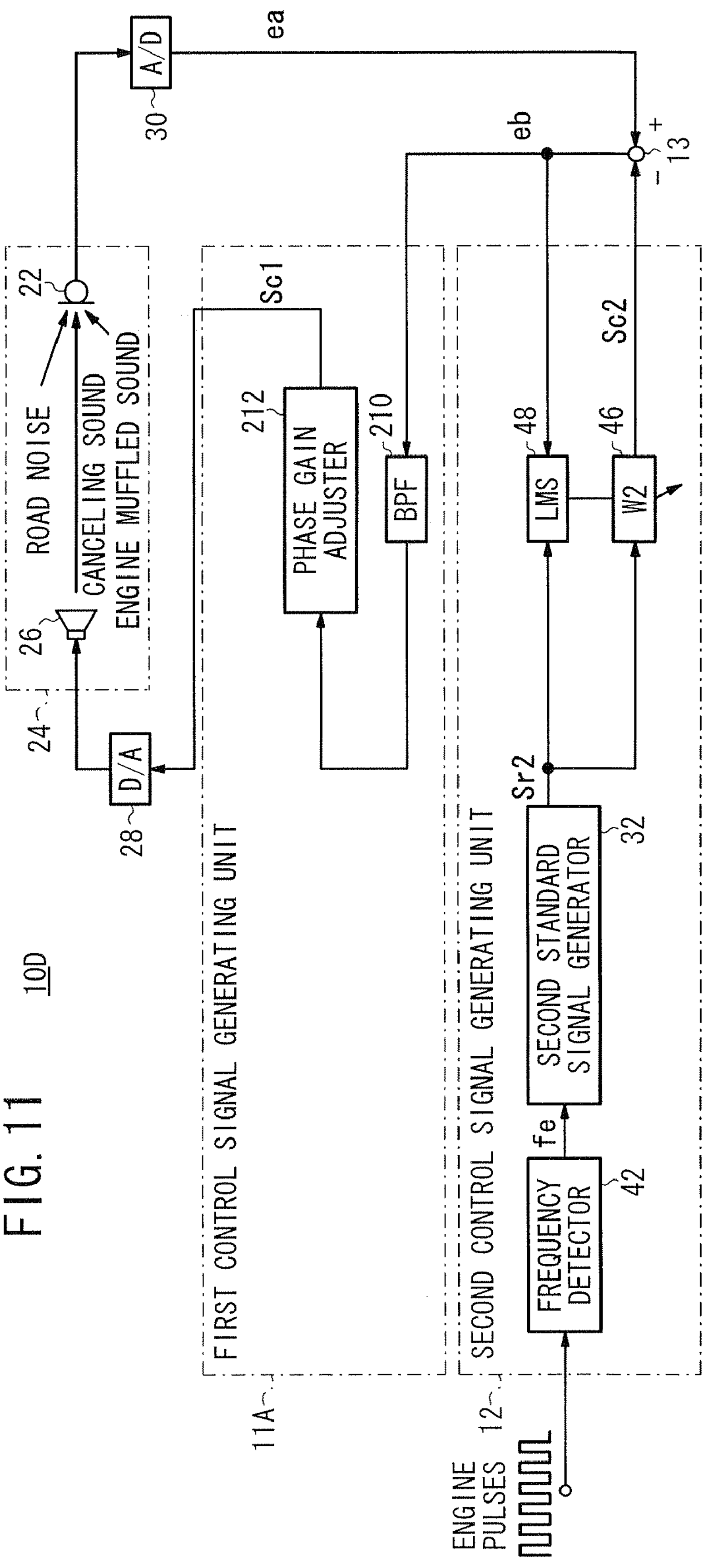
FIG. 11 is a block diagram showing a configuration of a vehicular active vibratory noise control apparatus according to a modification.

In all the above embodiments, the first control signal generating unit 11 may be modified into a first control signal generating unit 11A in a vehicular active vibratory noise control apparatus 10D according to a modification shown in FIG. 11. The first control signal generating unit 11A comprises a bandpass filter 210 whose passband has a central frequency of 42 [Hz] and a phase gain adjuster 212.

A phase delay θ1 and a gain G1, which are of fixed values, are set in the phase gain adjuster 212. The phase delay θ1 and the gain G1 may be determined in view of the fact that the canceling sound and the road noise need to have a phase difference of 180° (opposite phase) at the evaluating point and also to have the same amplitude in order to cause the road noise to be nil at the evaluating point where the microphone 22 is positioned. Specifically, the phase delay of a sine wave corresponding to the frequency f1=42 Hz of the road noise from the input point (position) of the microphone 22 through the A/D converter 30, the subtractor 13, the second control signal generating unit 12, the bandpass filter 210, the phase gain adjuster 212, the D/A converter 28, the speaker 26, and the in-compartment space 24 to the microphone 22 needs to be 180°, and the phase delay θ1 may have its fixed value set such that the phase delay will be 180°. The gain G1 may be considered in the same manner as with the phase delay θ1. In this case, the gain G1 may generally be set to a value (fixed value) which compensates for an attenuated value of the canceling sound in the path from the speaker 26 through the in-compartment space 24 to the microphone 22.

According to another modification, in all of the above embodiments, the second standard signal generator 32 may generate the second standard signals Sr2, Sr21 through Sr23 based on the standard frequency depending on the vehicle speed that is detected by a vehicle speed detector, not shown, used in place of the frequency detector 42 for detecting the rotational frequency fe of the engine crankshaft 64.

In the vehicular active vibratory noise control apparatus 10, 10A, 10B, 10C, 10D, the second control signal generating unit 12 and the subtractor 13 serve as a second control signal and corrected error signal generator for generating the second standard signal Sr2 relative to the rotating component mounted on the vehicle based on the rotational frequency fe of the rotating component, generating the second control signal Sc2 which is of the same amplitude as and in phase with the component of the engine muffled sound from the second standard signal Sr2 and the corrected error signal eb, and subtracting the second control signal Sc2 from the error signal ea to generate the corrected error signal eb.

The vehicular active vibratory noise control apparatus 10, 10A, 10B, 10C have the first control signal generating unit 11 for outputting the first control signal Sc1 based on the first standard signal Sr1 relative to the road noise and the corrected error signal eb, and the vehicular active vibratory noise control apparatus 10D has the first control signal generating unit 11A for outputting the first control signal Sc1 based on the corrected error signal eb.

Although certain preferred embodiments of the present invention have been shown and described in detail, it should be understood that various changes and modifications may be made therein without departing from the scope of the appended claims.

What is claimed is:

1. A vehicular active vibratory noise control apparatus comprising:

a first standard signal generator for generating a first standard signal relative to a road noise on a vehicle;

a first adaptive filter for outputting a first control signal based on said first standard signal;

a canceling sound output unit for outputting a canceling sound to cancel said road noise based on said first control signal;

an error signal detector for detecting a residual noise due to an interference between said canceling sound and said road noise at an evaluating point, as an error signal;

a first filter coefficient updater for sequentially updating a first filter coefficient of said first adaptive filter;

a rotational frequency detector for detecting a rotational frequency of a rotating component mounted on the vehicle;

a second standard signal generator for generating a second standard signal relative to said rotating component based on the detected rotational frequency;

a second adaptive filter for outputting a second control signal based on said second standard signal;

a second filter coefficient updater for sequentially updating a second filter coefficient of said second adaptive filter; and a subtractor for generating a corrected error signal by subtracting said second control signal from said error signal, wherein said first filter coefficient updater updates said first filter coefficient based on said corrected error signal and said first standard signal.

2. A vehicular active vibratory noise control apparatus according to claim 1, wherein said rotating component comprises at least one of an engine crankshaft, a transmission main shaft, a transmission countershaft, a drive shaft, and a propeller shaft on the vehicle.

3. A vehicular active vibratory noise control apparatus according to claim 1, wherein said second control signal stops being output based on said rotational frequency.

4. A vehicular active vibratory noise control apparatus according to claim 1, wherein said rotational frequency detector detects the rotational frequencies of a plurality of rotating components, and said second standard signal generator generates a plurality of second standard signals based on the detected rotational frequencies.

5. A vehicular active vibratory noise control apparatus comprising:

a first control signal generating unit for generating a first control signal based on a corrected error signal or based on a corrected error signal and a first standard signal;

a canceling sound output unit for outputting a canceling sound to cancel a road noise based on said first control signal;

an error signal detector for detecting a residual noise due to an interference between said road noise, said canceling sound, and an engine muffled sound at an evaluating point, as an error signal; and a second control signal and corrected error signal generator for generating a second standard signal relative to a rotating component on a vehicle based on a rotational frequency of said rotating component, generating a second control signal which is of the same amplitude as and in phase with a component of said engine muffled sound from said second standard signal and said corrected error signal, and subtracting said second control signal from said error signal to generate said corrected error signal.

* * * * *